US011937938B1

(12) United States Patent
Bianchi et al.

(10) Patent No.: US 11,937,938 B1
(45) Date of Patent: Mar. 26, 2024

(54) METHODS FOR ASSESSING SLEEP CONDITIONS

(71) Applicant: Apple Inc., Cupertino, CA (US)

(72) Inventors: Matt Travis Bianchi, Santa Cruz, CA (US); Alexander Mark Chan, San Carlos, CA (US); Fredrik J. Sannholm, Kirkkonummi (FI); Lifeng Miao, Los Altos, CA (US); Siddharth Khullar, San Jose, CA (US)

(73) Assignee: Apple Inc., Cupertino, CA (US)

( * ) Notice: Subject to any disclaimer, the term of this patent is extended or adjusted under 35 U.S.C. 154(b) by 459 days.

(21) Appl. No.: 16/912,706

(22) Filed: Jun. 25, 2020

Related U.S. Application Data

(60) Provisional application No. 62/879,399, filed on Jul. 26, 2019.

(51) Int. Cl.
*A61B 5/00* (2006.01)
*A61B 5/08* (2006.01)

(52) U.S. Cl.
CPC .......... *A61B 5/4818* (2013.01); *A61B 5/0826* (2013.01); *A61B 5/7257* (2013.01);
(Continued)

(58) Field of Classification Search
CPC ... A61B 5/4818; A61B 5/0826; A61B 5/7257; A61B 5/7267; A61B 5/7275;
(Continued)

(56) References Cited

U.S. PATENT DOCUMENTS 8,504,158 B2  8/2013 Karamanoglu et al.
10,130,306 B2  11/2018 Katra et al.
(Continued)

FOREIGN PATENT DOCUMENTS

WO  2004/112606 A1  12/2004

OTHER PUBLICATIONS

U.S. Food and Drug Administration, "Letter to Hancook Medical Inc. regarding Beddr 200 System, K190399" Aug. 5, 2019, Available online at: <https://www.accessdata.fda.gov/cdrh_docs/pdf19/K190399.pdf>, retrieved on Jul. 31, 2020, 3 pages.
(Continued)

*Primary Examiner* — Yi-Shan Yang
*Assistant Examiner* — Kyle W. Kretzer
(74) *Attorney, Agent, or Firm* — Kubota & Basol LLP

(57) ABSTRACT

Sleep conditions such as moderate-to-severe sleep apnea can be assessed using a multi-night assessments. A respiration signal (e.g., acquired from a sensor strip) can be processed via a computing device. The respiration signal can be segmented and the segments can be classified to identify one or more apnea/hypopnea events. In some examples, some of the segments can be normalized such that each segment input for classification can be of the same size. The identified one or more apnea/hypopnea events can be used to estimate a nightly parameter indicative of a severity of (or presence of) sleep apnea. The nightly parameters from a multi-night period can be used to estimate a multi-night parameter indicative of the severity of (or presence of) sleep apnea. In some examples, quality checks can be performed to filter out some data (e.g., to exclude data from entire nights or exclude a portion of data from individual nights).

23 Claims, 8 Drawing Sheets

(52) U.S. Cl.
CPC .......... *A61B 5/7264* (2013.01); *A61B 5/7267* (2013.01); *A61B 5/7275* (2013.01); *A61B 5/742* (2013.01); *A61B 5/6892* (2013.01); *A61B 2562/0247* (2013.01)

(58) Field of Classification Search
CPC .................. A61B 5/742; A61B 5/6892; A61B 2562/0247; A61B 5/7264; A61B 5/4806
See application file for complete search history.

(56) References Cited

U.S. PATENT DOCUMENTS

| | | | |
|---|---|---|---|
| 2008/0177195 A1* | 7/2008 | Armitstead | A61B 5/4818 600/529 |
| 2011/0046498 A1* | 2/2011 | Klap | A61B 5/6887 600/534 |
| 2011/0061647 A1 | 3/2011 | Stahmann et al. | |
| 2011/0251985 A1* | 10/2011 | Waxman | A61B 5/7275 706/20 |
| 2013/0060150 A1 | 3/2013 | Song et al. | |
| 2014/0171815 A1 | 6/2014 | Yang et al. | |
| 2014/0323919 A1* | 10/2014 | Tsutsumi | A61B 7/003 600/586 |
| 2015/0157258 A1* | 6/2015 | Beattie | A61B 5/113 600/534 |
| 2015/0282738 A1* | 10/2015 | Thakur | A61B 5/02405 600/528 |
| 2016/0045161 A1 | 2/2016 | Alshaer et al. | |
| 2016/0287122 A1 | 10/2016 | Heneghan | |
| 2017/0055898 A1* | 3/2017 | Bandyopadhyay | A61B 5/303 |
| 2019/0374167 A1* | 12/2019 | Won | A61B 7/003 |

OTHER PUBLICATIONS

U.S. Food and Drug Administration, "Letter to Resonea, Inc. regarding Drowzle Sleep Apnea Prescreening Device, K173974", Jul. 14, 2019, Available online at: <https://www.accessdata.fda.gov/cdrh_docs/pdf17/K173974.pdf>, retrieved on Jul. 31, 2020, 9 pages.

McGarry, Caitlin, "Fitbit Really Wants to Be Able to Diagnose Your Sleep Apnea", GIZMODO, Jan. 15, 2020, Available online at: <https://gizmodo.com/fitbit-really-wants-to-be-able-to-diagnose-your-sleep-a-1841027997>, retrieved on Jul. 27, 2020, 4 pages.

Resapp Health Limited, "SleepCheck App for iPhone Now Available on the App Store", Brisbane, Australia, Jun. 29, 2020, Available online at: <https://www.resapphealth.com.au/sleepcheck-app-for-iphone-now-available-on-the-app-store/>, retrieved on Jul. 27, 2020, 4 pages.

Stein, Scott, "Withings' New Health Watch Can Check for Sleep Apnea", CNET Health and Wellness, Jan. 5, 2020, Available online at: <https://www.cnet.com/health/withings-new-smartwatch-can-check-for-sleep-apnea/>, retrieved on Jul. 27, 2020, 4 pages.

Withings, "Sleep / Sleep Analyzer—Tracking My Sleep Apnea", Available online at: <https://support.withings.com/hc/en-us/articles/360007808398-Sleep-Sleep-Analyzer-Tracking-my-sleep-apnea>, retrieved on Jul. 27, 2020, 4 pages.

* cited by examiner

METHODS FOR ASSESSING SLEEP CONDITIONS

CROSS REFERENCE TO RELATED APPLICATIONS

This application claims the benefit under 35 U.S.C. 119(e) of U.S. Provisional Patent Application No. 62/879,399, filed Jul. 26, 2019, the content of which is incorporated herein by reference in its entirety for all purposes.

FIELD

This relates generally to systems and methods for assessing sleep conditions, and more particularly, to detection of individual respiratory events and performing multi-night assessments.

BACKGROUND

Sound sleep has always been considered vital for health. Abnormal sleep habits may lead to many health disorders. Some sleep disorders may adversely affect the physical and psychological functioning of human body. Accordingly, various devices and tests are available for detecting, monitoring and/or recording sleep parameters.

In some examples, sleep can be monitored using multiple sensor devices in proximity with a user. In some examples, the one or more sensor devices can be in communication with a computing device, which can process data from the one or more sensor devices and make a determination based on the data. For example, the sleep state (e.g., awake or asleep) of a user can be determined based on the data. In some examples, the onset of sleep can be deduced based on the data from the one or more sensor devices. As described herein, it may also be useful to detect additional information regarding sleep conditions beyond the sleep state, such as information about respiration during sleep (e.g., apnea/hypopnea events).

SUMMARY

This relates to systems and methods for assessing sleep conditions, and more particularly, to detection of individual breathing events (e.g., apnea/hypopnea events) and performing multi-night assessments (e.g., to screen for moderate-to-severe sleep apnea or other classifications of respiration). In some examples, a respiration signal can be acquired from a sensor strip (e.g., a sensor strip including one or more piezoelectric sensors placed underneath a sheet or mattress of the user) and processed via a computing device to enable screening for sleep apnea. The less-invasive screening (e.g., using the sensor strip described herein) can provide an estimate of a degree of sleep apnea that can be used as preliminary step before further, more-invasive steps (e.g., with multiple sensor types including electroencephalogram (EEG) sensor(s), airflow sensor(s), effort belt sensor(s) and pulse oximeter(s)) can be taken to diagnose the sleep apnea condition.

The respiration signal can be segmented and the segments can be classified to identify one or more apnea/hypopnea events. In some examples, some of the segments can be normalized (by up-sampling and/or down-sampling) such that each segment input for classification can be of the same size. The segments may also be normalized in amplitude, in some examples. The identified one or more apnea/hypopnea events can be used to estimate a nightly parameter indicative of a severity of (or presence of) sleep apnea. The nightly parameters from a multi-night period can be used to estimate a multi-night parameter indicative of the severity of (or presence of) sleep apnea.

In some examples, the respiration signal is segmented and a frequency domain representation of the segments is computed. An input image can be generated from the frequency domain representations of the segments. A machine learning model can be applied to the input to classify the segments to identify one or more apnea/hypopnea events. The identified one or more apnea/hypopnea events can be used to estimate a nightly parameter indicative of a severity of (or presence of) sleep apnea. The nightly parameters from a multi-night period can be used to estimate a multi-night parameter indicative of the severity of (or presence of) sleep apnea.

In some examples, to improve the multi-night assessment, quality checks can be performed to filter out some data (e.g., to exclude data from entire nights or exclude a portion of the data from individual nights). The quality checks can include requiring one or more criteria be met. In some examples, the quality checks can include a criterion related to respiration signal amplitude. In some examples, the quality checks can include a criterion related to noise in the respiration signal. In some examples, the quality checks can include a criterion related to continuity of respiration signal quality.

DETAILED DESCRIPTION

Figure 1A:
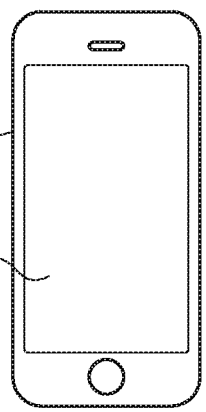
FIGS. 1A-1F illustrate example systems that can be used to assess sleep conditions according to examples of the disclosure and an example sensor device according to examples of the disclosure.

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

This relates to systems and methods for assessing sleep conditions, and more particularly, to detection of individual breathing events (e.g., apnea/hypopnea events) and performing multi-night assessments (e.g., to screen for moderate-to-severe sleep apnea or other classifications of respiration). In some examples, a respiration signal can be acquired from a sensor strip (e.g., a sensor strip including one or more piezoelectric sensors placed underneath a sheet or mattress of the user) and processed via a computing device to enable screening for sleep apnea. The less-invasive screening (e.g., using the sensor strip described herein) can provide an estimate of a degree of sleep apnea that can be used as preliminary step before further, more-invasive steps (e.g., with multiple sensor types including electroencephalogram (EEG) sensor(s), airflow sensor(s), effort belt sensor(s) and pulse oximeter(s)) can be taken to diagnose the sleep apnea condition.

The respiration signal can be segmented and the segments can be classified to identify one or more apnea/hypopnea events. In some examples, some of the segments can be normalized (by up-sampling and/or down-sampling) such that each segment input for classification can be of the same size. The segments may also be normalized in amplitude, in some examples. The identified one or more apnea/hypopnea events can be used to estimate a nightly parameter indicative of a severity of (or presence of) sleep apnea. The nightly parameters from a multi-night period can be used to estimate a multi-night parameter indicative of the severity of (or presence of) sleep apnea.

In some examples, the respiration signal is segmented and a frequency domain representation of the segments is computed. An input image can be generated from the frequency domain representations of the segments. A machine learning model can be applied to the input to classify the segments to identify one or more apnea/hypopnea events. The identified one or more apnea/hypopnea events can be used to estimate a nightly parameter indicative of a severity of (or presence of) sleep apnea. The nightly parameters from a multi-night period can be used to estimate a multi-night parameter indicative of the severity of (or presence of) sleep apnea.

In some examples, to improve the multi-night assessment, quality checks can be performed to filter out some data (e.g., to exclude data from entire nights or exclude a portion of the data from individual nights). The quality checks can include requiring one or more criteria be met. In some examples, the quality checks can include a criterion related to respiration signal amplitude. In some examples, the quality checks can include a criterion related to noise in the respiration signal. In some examples, the quality checks can include a criterion related to continuity of respiration signal quality.

Figure 1B:
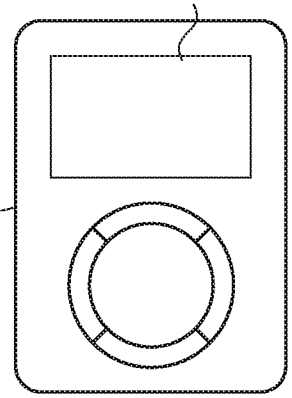
Figure 1C:
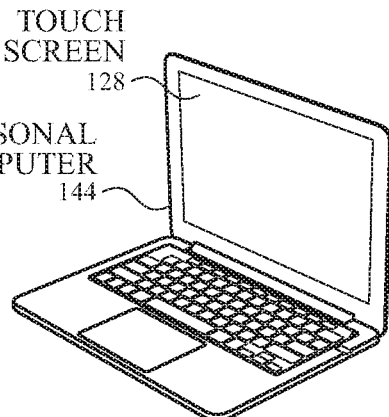
Figure 1D:
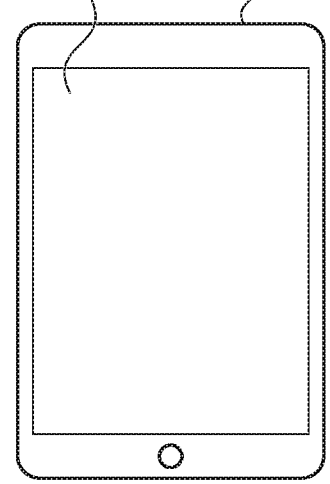
Figure 1E:
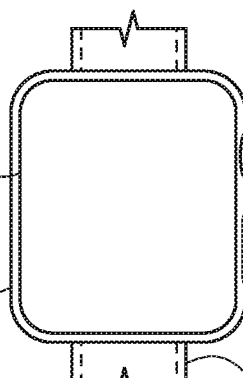

FIGS. 1A-1F illustrate example systems that can be used to assess sleep conditions according to examples of the disclosure and an example sensor device according to examples of the disclosure. FIG. 1A illustrates an example mobile telephone 136 that includes a touch screen 124 that can assess sleep conditions according to examples of the disclosure. FIG. 1B illustrates an example digital media player 140 that includes a touch screen 126 that can assess sleep conditions according to examples of the disclosure. FIG. 1C illustrates an example personal computer 144 that includes a touch screen 128 that can assess sleep conditions according to examples of the disclosure. FIG. 1D illustrates an example tablet computing device 148 that includes a touch screen 130 that can assess sleep conditions according to examples of the disclosure. FIG. 1E illustrates an example wearable device 150 that includes a touch screen 132 and can be attached to a user using a strap 152 and that can assess sleep conditions according to examples of the disclosure. It is understood that assessing sleep conditions according to examples of the disclosure can be implemented in other devices as well. Additionally it should be understood that although the systems of FIGS. 1A-1E include touch screens, assessing sleep conditions can be implemented devices without a touch screen or a display.

Figure 1F:
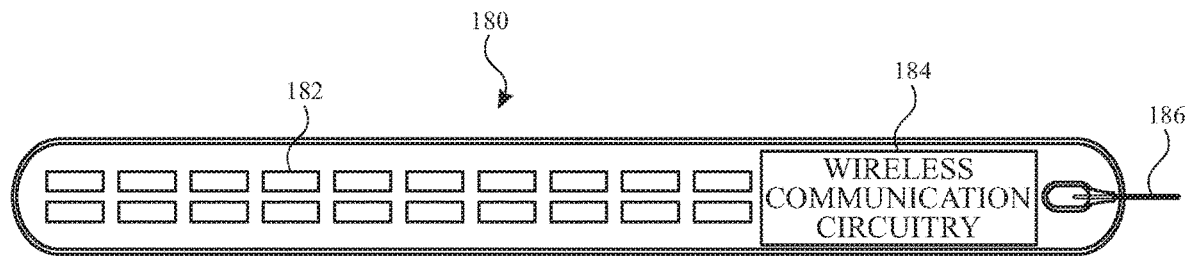
Figure 2:
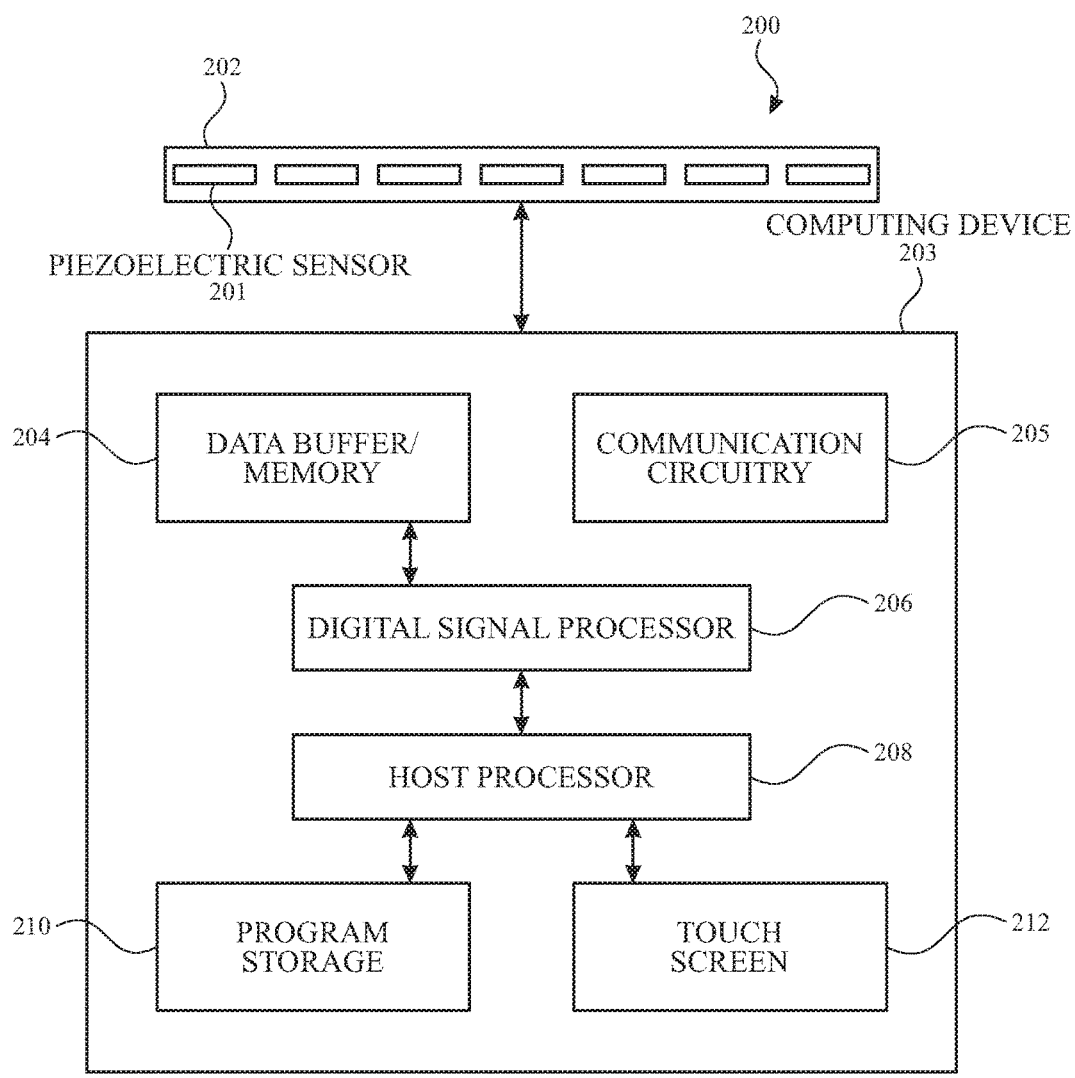
FIG. 2 illustrates a block diagram of an example system that illustrates one implementation of a physiological sensor device and physiological signal processing according to examples of the disclosure.

FIG. 1F illustrates an example sensor device according to examples of the disclosure. Sensor strip 180 can include one or more piezoelectric sensors 182 configured to acquire physiological signals. In some examples, the piezoelectric sensors 182 can be arranged in a one-dimensional (e.g., as shown in FIG. 2) or a multi-dimensional array (e.g., as shown in FIG. 1F). In some examples, a single piezoelectric sensor can be used. The piezoelectric sensor can detect motion signals (e.g., due to respiration, heartbeats, blood pressure, body movements, etc.). In some examples, the piezoelectric sensors can be formed as a thin-film sensor. In some examples, each of the one or more piezoelectric sensors 182 can include a crystal and when the crystal deforms under a mechanical load, the crystal can redistribute its electric charge to its surroundings. This piezoelectric effect can be used to measure, e.g., pressure, acceleration, strain or force. In some examples, the sensor strip 180 can be installed at a surface of a deformable object, such as a mattress, and can be used for measuring the amount of deformation of the object when experiencing a mechanical load. Sensor strip 180 can be powered via a wired connection 186. In some examples, sensor strip 180 can include a battery that can be charged via wired connection 186 or wirelessly (e.g., via inductive charging).

In some examples, the piezoelectric sensors 182 can be arranged on the elastic fabric of a user's mattress in such a way that movements of the user's chest due to heartbeat and/or respiration can cause a mechanical stress on the piezoelectric sensors. The signal originating from these piezoelectric sensors can be used to monitor physiological signals (e.g., heartbeat and/or respiration). The piezoelectric effect can be measured by measurement circuitry (not shown). The measurement circuitry can include an amplifier to measure changes in the piezoelectric material of the piezoelectric sensor. For example, the amplifier can measure a change in voltage (or a current) corresponding to the applied force from the user's respiration. The measurement circuitry can also include an analog-to-digital converter (ADC) to convert the analog signals output by the amplifier to a digital signal for processing.

The physiological signals can be processed to detect physiological conditions and to assess sleep conditions as described herein. In some examples, the physiological signals (e.g., a respiration signal) can be communicated from sensor strip 180 to a processing device (e.g., mobile telephone 136, digital media player 140, personal computer 144, tablet computing device 148, wearable device 150, etc.). In some examples, the physiological signals can be communicated wirelessly by wireless communication circuitry 184 (e.g., WiFi or Bluetooth chip). In some examples, the physiological signals can be stored in a memory (not shown) within sensor strip 180. In some examples, the physiological signal can be communicated to the processing device via a wired connection (e.g., via a universal serial bus cable). In some examples, the processing of the physiological signal can be performed in part or in whole by processing circuitry within sensor strip 180. In some examples, the processing can be performed by two or more processing devices.

In some examples, the piezoelectric sensor can be implemented using a piezoelectric film. The piezoelectric film can be stimulated by a power source, which can cause the piezoelectric film to vibrate. In some examples, the piezoelectric film can be driven with alternating voltage or current at a frequency in the range of 30-60 kHz. The piezoelectric film can be integrated into the sensor strip 180 to induce movement in the thin film of the piezoelectric thin film sensors, when stimulated by the alternating voltage or current. The motional resistance of the moving piezoelectric sensor changes when moving freely compared with when the body of a person rests on the piezoelectric sensor. The weight of the person can cause damping in the motion, which can be measured as an indication of a physiological signal (e.g., a respiration signal).

Although sensor strip 180 is described as including only piezoelectric sensors, in some examples, additional and/or different sensors can be used to monitor one or more physiological signal. For example, the piezoelectric sensors, in some examples, can be augmented with additional sensors including one or more strain gauges, capacitive sensors, proximity sensors, thermocouples, inductive sensors, accelerometers, gyroscopes, etc. In some examples, the one or more additional sensors can be implemented separate from sensor strip 180. For example, one or more physiological sensors can be implemented in wearable device 150 and can be used to measure physiological signals (e.g., heart rate, electrocardiogram, pulse oximetry, etc.) of a user.

FIG. 2 illustrates a block diagram of an example system 200 that illustrates one implementation of a physiological sensor device and physiological signal processing according to examples of the disclosure. System 200 can include one or more physiological sensors and a computing device 203. Computing device 203 can be included in, for example, mobile telephone 136, digital media player 140, personal computer 144, tablet computing device 148, wearable device 150, or any mobile or non-mobile, wearable or non-wearable computing device for physiological signal analysis and/or display. System 200 can include one or more physiological sensors, such as piezoelectric sensors 201, to measure physiological signals from a person sleeping on the one or more physiological sensors. For example, FIG. 2 illustrates a sensor strip 202 including one or more piezoelectric sensors 201 (e.g., corresponding to sensor strip 180). Computing device 203 can include communication circuitry 205 to receive physiological signals from sensor strip 202 (e.g., via a wired or wireless connection). Computing device 203 can include a data buffer 204 (or other volatile or non-volatile memory or storage) to store temporarily (or permanently) the physiological signals from the physiological sensors 202, digital signal processor (DSP) 206 to analyze and process the physiological signals, host processor 208, program storage 210, and touch screen 212 to perform display operations (e.g., to display results of the sleep condition assessment). In some examples, touch screen 212 may be replaced by a non-touch sensitive display or the touch and/or display functionality can be implemented in another device.

Host processor 208 can be connected to program storage 210 to execute instructions stored in program storage 210 (e.g., a non-transitory computer-readable storage medium). Host processor 208, for example, can provide control and data signals to generate a display image on touch screen 212, such as a display image of a user interface (UI). Host processor 208 can also receive outputs from DSP 206 (e.g., a sleep assessment) and performing actions based on the outputs (e.g., display the sleep assessment, play a sound, provide haptic or other feedback, etc.). Host processor 208 can also receive touch input from touch screen 212 (or a touch controller, not shown). The touch input can be used by computer programs stored in program storage 210 to perform actions that can include, but are not limited to, moving an object such as a cursor or pointer, scrolling or panning, adjusting control settings, opening a file or document, viewing a menu, making a selection, executing instructions, operating a peripheral device connected to the host device, answering a telephone call, placing a telephone call, terminating a telephone call, changing the volume or audio settings, storing information related to telephone communications such as addresses, frequently dialed numbers, received calls, missed calls, logging onto a computer or a computer network, permitting authorized individuals access to restricted areas of the computer or computer network, loading a user profile associated with a user's preferred arrangement of the computer desktop, permitting access to web content, launching a particular program, encrypting or decoding a message, and/or the like. Host processor 220 can also perform additional functions that may not be related to touch processing and display. In some examples, host processor 220 can perform some of the signal processing functions described herein.

Note that one or more of the functions described herein, including the processing of physiological signals to assess sleep conditions, can be performed by firmware stored in memory (e.g., in DSP 206) and executed by one or more processors (in DSP 206), or stored in program storage 210 and executed by host processor 208. The firmware can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

It is to be understood that the system 200 is not limited to the components and configuration of FIG. 2, but can include other or additional components (or omit components) in multiple configurations according to various examples. Additionally, the components of system 200 can be included within a single device, or can be distributed between multiple devices.

Physiological sensor(s) in sensor strip 202 can be in communication with DSP 206 to acquire physiological signals and transmit the physiological signals to DSP 206. In some examples, the physiological signals can be a respiration signal stored in data buffer 204 and the DSP 206 can acquire a buffered sample. In some examples, data buffer 204 can be implemented as part of DSP 206. It should be understood that although a DSP is described, other processing circuits could be used to implement the analysis and processing described herein including a microprocessor, central processing unit (CPU), programmable logic device (PLD), and/or the like.

Conventionally, diagnosing sleep apnea requires a patient to spend one or more nights in a sleep laboratory (or at home with a home sleep apnea testing kit), wearing various sensors including electroencephalogram sensors, airflow sensors, respiratory effort sensors and a pulse oximetry sensor. The use of sensor strip 202 and computing device 203 can provide an early screening for undiagnosed sleep apnea (e.g., moderate/severe) without the more invasive sensors required for a proper diagnosis. If the screening estimates an undiagnosed sleep apnea (e.g., moderate or severe sleep apnea) for a user, the user can then undergo more invasive testing to diagnose the sleep apnea condition. As described herein, the assessing sleep conditions can include screening for a sleep apnea condition. In some examples, the screening output can be a binary result. For example, the screening can provide an indication for a user to seek a proper sleep apnea diagnosis in a sleep laboratory (or at home with a home sleep apnea testing kit) or not. In some examples, the screening can be for moderate-to-severe sleep apnea condition, and the moderate or severe sleep apnea condition can provide the indication for a user to seek a proper sleep apnea diagnosis (whereas less than a moderate sleep apnea condition may not provide such an indication). In some examples, the screen can be for a sleep apnea level. In some cases, the sleep apnea levels can include a mild sleep apnea condition, a moderate sleep apnea condition and/or a severe sleep apnea condition. In some examples, the sleep apnea level can include a level corresponding to no sleep apnea condition.

The screening for moderate or severe sleep apnea condition can include collecting and processing a physiological signal (e.g., respiration signal) across multiple time periods corresponding to multiple sleep sessions across multiple days. In some examples, multiple time periods can correspond to nights of sleep. In some examples, the duration of the screening can include measuring sleeping conditions for at least a minimum number of nights. In some examples, the minimum number of nights can be 14 nights, though a smaller or larger minimum number of nights may be used (e.g., 5, 7, 10, 21, etc.). In some examples, the duration of the screening can include measuring sleeping conditions for no more than a maximum number of nights. In some examples, the maximum number of nights can be 30 nights, though a smaller or larger maximum number may be used (e.g. 25, 35, 40, etc.). In some examples, the screening can include data from a minimum number of qualifying nights of sleep among the measured nights (as described in more detail herein). In some examples, the minimum number of qualifying nights of sleep can be 14 qualifying nights of sleep, though a smaller or larger minimum number of qualifying nights of sleep may be use (e.g., 7-21 qualifying nights of sleep). It should be understood that although primarily referred to herein as nights of sleep, the screening can be performed during other periods of time. For example, a person with an inverted sleep pattern (sleeping during nights and awake during days) may be screened based on sleep sessions that occur across multiple days, rather than nights.

Figure 3A:
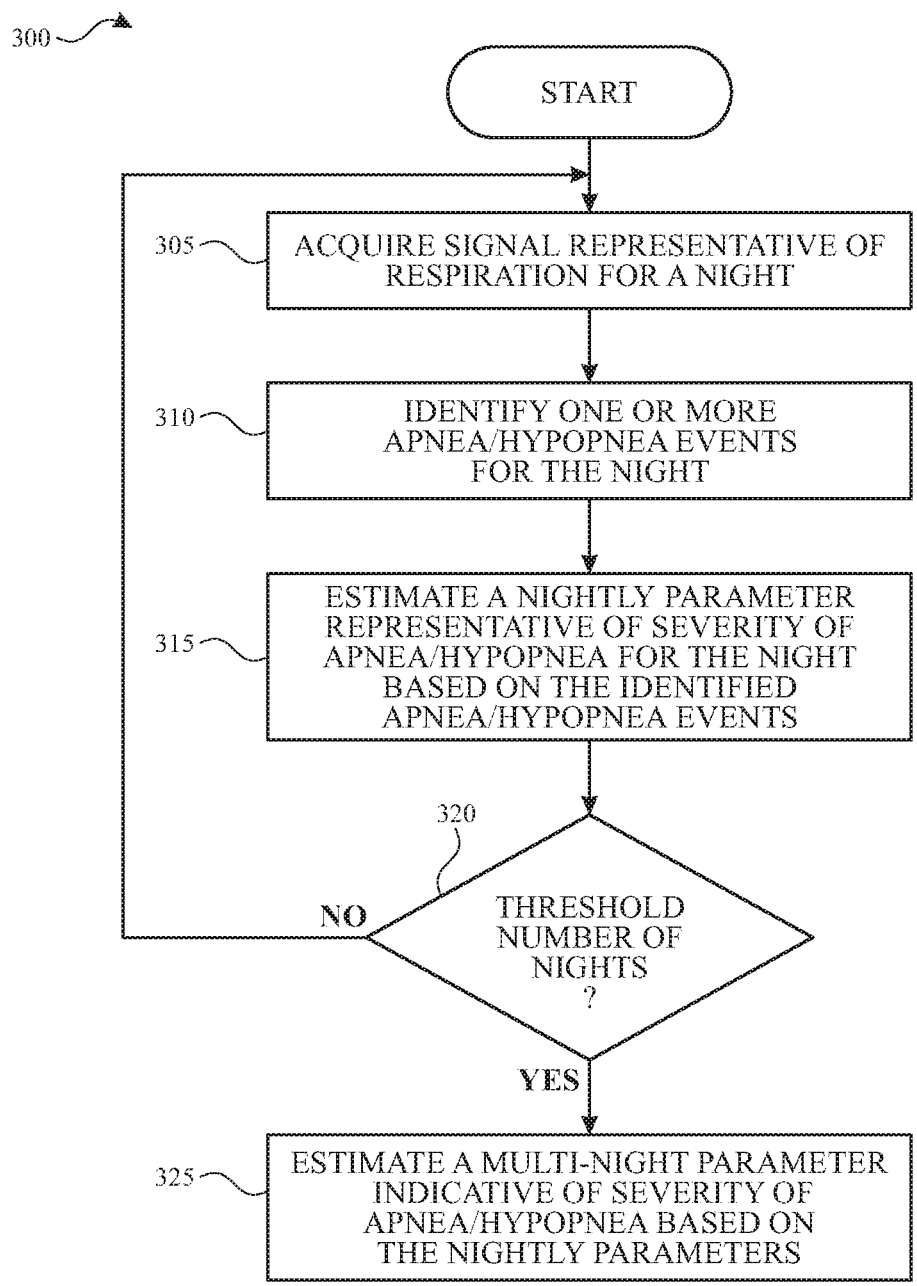
FIG. 3A illustrates an exemplary process for assessing a sleep condition according to examples of the disclosure.

FIG. 3A illustrates an exemplary process 300 for assessing a sleep condition according to examples of the disclosure. In some examples, the sleep condition can be sleep apnea condition and assessing the sleep condition can include a sleep apnea screening for undiagnosed cases of sleep apnea based on multiple sleep sessions conducted over the course of a period of several nights (or days).

Process 300 can begin with, at 305, the acquisition of a signal representative of respiration of a user. In some examples, the signal representative of the respiration of the user (often referred to herein as a "respiration signal") can be measured by one or more sensors, such as piezoelectric sensors 182/201 described above with reference to FIGS. 1F and 2, or any other suitable sensor(s). The respiration signal can be sensed as an analog, continuous time domain signal by the one or more sensors, and in some examples, the respiration signal can be digitized into a digital signal by an analog-to-digital converter (ADC). The respiration signal can be stored in digital form in data buffer/memory 204 or the respiration signal can be supplied directly to digital signal processor 206. In some examples, the respiration signal can be acquired during periods of time corresponding to sleep during a night between two calendar days. In some examples, the acquisition of the respiration signal can be triggered by a user beginning a sleep apnea screening process (e.g., in an application on a computing device, such as mobile telephone 136, etc.). In some examples, the acquisition of the respiration signal can be performed during other sleep periods rather than during the night. In some examples, the acquisition of the respiration signal can occur (or the respiration signal can be used or saved) while the system detects a user (e.g., using sensor strip 180/202), and the acquisition of the respiration signal can pause or cease (or the respiration signal can be ignored or discarded) while the system does not detect a user. In some examples, the acquisition of the respiration signal can occur (or the respiration signal can be used or saved) while the system detects the user sleeping (e.g., using sensor strip 180/202), and the acquisition of the respiration signal can pause or cease (or the respiration signal can be ignored or discarded) while the system does not detect the user sleeping.

At 310, the respiration signal can be processed to identify one or more apnea/hypopnea events. The details of apnea/hypopnea event identification are described below with reference to process 400 or process 402.

At 315, a parameter can be estimated for a night (or other period of sleep) based on the identified apnea/hypopnea events for the corresponding night. This parameter can be referred to herein as a "nightly parameter." In some examples, the nightly parameter can be represented with a state. For example, the nightly parameter can be a "normal" (non-sleep apnea) state, "mild sleep apnea" state, "moderate sleep apnea state" or "severe sleep apnea" state. These states can be delineated based on a number of apnea/hypopnea events (e.g., apnea/hypopnea events per hour of sleep for a night) using an index of apnea/hypopnea events (e.g., an apnea-hypopnea index). For example, different thresholds can separate between the corresponding states (e.g., less than a first threshold number of apnea/hypopnea events corresponds to a "normal state", between the first threshold and a second threshold corresponds to a "mild" state, between the second threshold and a third threshold corresponds to a "moderate" state, and above the third threshold corresponds to a "severe" state). In some examples, the nightly parameter can be further simplified and can be represented with a binary state designation as "moderate-to-severe apnea" (when the number of apnea/hypopnea events exceeds a threshold) or "not moderate-to-severe apnea" (when the number of apnea/hypopnea events does not exceed the threshold). In such examples, the final output of the multi-night assessment can similarly be a reporting of state as moderate-to-severe apnea or not. In some examples, the nightly parameter can be a continuous variable representing the apnea/hypopnea events for the corresponding night. For example, the number of apnea/hypopnea events during sleep for a night can be summed and divided by time of sleep (time of recording) to determine a rate of apnea/hypopnea events (e.g., apnea/hypopnea event per hour). The value of the continuous variable can be the rate of apnea/hypopnea.

When nightly parameters for less than a threshold number of nights have been estimated (320), the processing at 305, 310 and 315 can be repeated for an additional night. When nightly parameters for a threshold number of nights have been estimated (320), a parameter can be estimated for a multi-night period based on the estimated nightly parameters at 325. This parameter can be referred to herein as a "multi-night parameter." In order to improve the confidence in the assessment of the sleep apnea condition, the acquisition of respiration signals at 305, the identification of apnea/hypopnea events at 310 and the nightly parameter estimation at 315 can be repeated for multiple nights (rather than a single night). Each nightly parameter can be view as an imperfect classifier and the multi-night parameter can be viewed as daisy-chaining multiple imperfect classifiers. In some examples, the nightly parameter can be a continuous variable and the multi-night parameter can be calculated by averaging the nightly parameter for each night across the multi-night period. In some examples, the continuous variable can then be used to determine the screening result (e.g., sleep apnea severity) by comparing the continuous variable to thresholds separating between the corresponding states (e.g., as described above with respect to the nightly parameter). It should be understood that these descriptions of estimating the multi-night parameter are some examples of daisy-chaining the nightly parameters, but that other possibilities are within the scope of the disclosure. For example, a weighted average (e.g., weighted based on a confidence for a particular nightly parameter), a mode, or a median value of the continuous variable can be used rather than a mean. In some examples, the nightly parameter can be a state, and the multi-night parameter can be state determined based on the nightly parameters estimated across the multi-night period. For example, using a binary-state nightly parameter, the multi-night parameter can be a "moderate-to-severe apnea" state when a threshold number of nightly parameters in the multi-night period correspond to a "moderate-to-severe apnea" state. When fewer than the threshold number of nightly parameters in the multi-night period correspond to the "moderate-to-severe apnea" state, the multi-night parameter can be a "not moderate-to-severe apnea" state.

The number of nights in the multi-night period can be selected in order to build accuracy (e.g., by effectively daisy-chaining together multiple imperfect nightly classifiers). In some examples, the number of nights in the multi-night period can be 7 nights (e.g., to include both weeknights and weekend nights). In some examples, the number of nights in the multi-night period can be greater than 7 nights (e.g., 10 nights, 14 nights, 20 nights, etc.) or less than 7 nights (e.g., 2, 3, 5, etc.). In some examples, the number of nights can be selected based on characteristics of the user. For example, a first user can have a first number of nights required for the multi-night period and a second user can have a second number of nights required for the multi-night period. In some examples, the number of nights for different users may depend on other information about the user including age, prior sleep assessments by the screening methods described herein, and/or other medical information.

The description of process 300 above may assume that the respiration signal and subsequent processing for each night in the multi-night period should be used for the multi-night assessment. However, in practice not all nights of sleep may be of sufficient quality to be used in making an accurate assessment. In some examples, a threshold number of qualifying nights can be required for a multi-night period as described in more detail with relation to process 350. Non-qualifying nights can be excluded from the assessment.

Figure 3B:
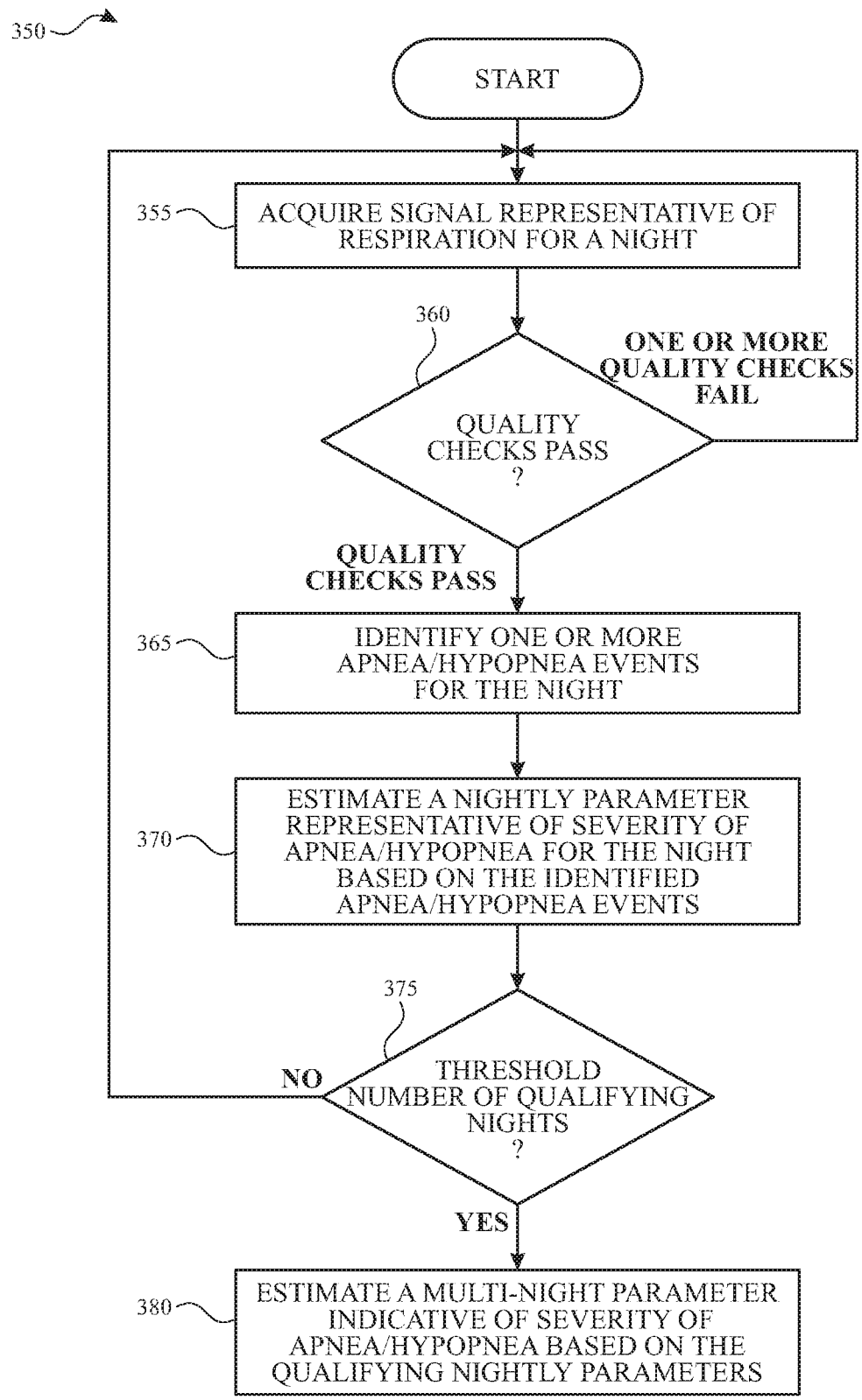
FIG. 3B illustrates another exemplary process for assessing a sleep condition according to examples of the disclosure.

FIG. 3B illustrates another exemplary process 350 for assessing a sleep condition according to examples of the disclosure. Process 350 can begin with, at 355, the acquisition of a signal representative of respiration of a user (corresponding to the acquisition of a respiration signal at 305 in process 300). At 360, one or more quality checks can be performed and a determination can be made about whether the quality checks pass or fail. The quality checks can include, for example, determining whether qualifying criteria are met for the respiration signal. In some examples, the quality checks can include a criterion related to respiration signal amplitude. In some examples, the quality checks can include a criterion related to noise in the respiration signal. In some examples, the quality checks can include a criterion related to the signal-to-noise ratio of the respiration signal. In some examples, the quality checks can include a criterion related to continuity of respiration signal quality. The one or more quality checks are described in more detail below with respect to process 500.

When quality checks pass, the processing for a night can occur, and at 365, the respiration signal can be processed to identify one or more apnea/hypopnea events (corresponding to the processing to identify one or more apnea/hypopnea events at 310 and described below with reference to process 400 or process 402). At 370, a nightly parameter can be estimated for the qualifying night based on the identified apnea/hypopnea events for the corresponding night (corresponding to the processing at 315 of process 300). When quality checks fail, the processing of the data to identify one or more apnea/hypopnea events and estimate the nightly parameter can be skipped for the non-qualifying night. When nightly parameters for less than a threshold number of qualifying nights have been estimated (375), the processing at 355, 360, 365, and possibly 370 can be repeated for an additional night. When nightly parameters for a threshold number of qualifying nights have been estimated (375), a multi-night parameter can be estimated for a multi-night period based on the estimated nightly parameters for qualifying nights at 380.

The processing at 380 can be similar to the processing at 325, but considering the data from qualifying nights. For example, a multi-night continuous variable can be estimated based on the continuous variable estimated for each qualifying night (e.g., weighted or unweighted mean, mode, median, etc.) or the multi-night state can be estimated based on the estimated states for each qualifying night.

The threshold number of qualifying nights can be the same number of number of nights as described above. The screening processes can estimate nightly parameters for qualifying nights and not estimate parameters for not qualifying nights, until the threshold number of nights are qualifying. In some examples, the screening can require the threshold number of nights be achieved within a maximum number of nights. For example, the screening can require the number of qualifying nights (e.g., 7, 10, 14, 15, 21 etc.) be achieved within a maximum number of nights (e.g., 21, 28, 30, etc.).

In some examples, the quality checks can include an additional criterion based on user input. For example, a user can be prompted (e.g., upon waking up or at the conclusion of the screening period, etc.) to classify a night of sleep as typical or atypical. Atypical nights of sleep can be considered non-qualifying. In some examples, user input can be ignored for quality checks for individual nights, but the user input can be used to identify certain atypical sleep conditions that can be used to determine whether to terminate and/or reset the screening process (e.g., changes in medication, stress events, etc.)

Although quality checks are performed in exemplary process 350 before identifying one or more apnea/hypopnea events at 365 and estimating a nightly parameter at 370, it should be understood that quality checks can be implemented in other ways. For example, quality checks can be performed after identifying one or more apnea/hypopnea events at 365 and/or after estimating a nightly parameter at 370, and the identified one or more apnea/hypopnea events and/or the nightly parameter (and/or the respiration signal) for a non-qualifying night can be discarded or ignored. In some examples, the signal quality checks can be divided into multiple stages. For example, some quality checks (e.g., signal check and noise check) can be performed prior to identifying the one or more apnea/hypopnea events at 365 (e.g., prior to classification at 445 in process 400 or classification at 476 in process 402). For example, if the respiration signal fails to meet signal and noise quality checks, the processing to identify apnea/hypopnea events can be bypassed for those portions of the night (or for the entire night). Subsequently, after identifying the one or more apnea/hypopnea events at 365 or after estimating the nightly parameter at 370, some quality checks (e.g., continuity of signal quality) can be performed to determine whether to estimate or keep the nightly parameter at all. It should be understood that other variations to process 300 and 350 are possible and within the scope of the disclosure.

After estimating a multi-night parameter, the multi-night parameter can be reported to the user. In some examples, the user can receive feedback indicating a binary state. For example, the output (e.g., on the display screen) could be a "high-risk" of moderate-to-severe sleep apnea or a "low-risk" of moderate-to-severe sleep apnea. Along with a "high risk" result, the user can be prompted to take one or more actions including seeking out a medical professional to confirm the diagnosis. In some examples, the result (and a report including data) can be shared automatically (or manually) with the medical professional. In some examples, along with a "low risk" result, the user can be prompted to perform a new screening for sleep apnea after a predetermined period of time (e.g., after 3 months, after 6-months, etc.). In some examples, the period of time can be a function of the screening. For example, a "mild sleep apnea" result could trigger an earlier prompt than a "normal" result. In some examples, the period of time can be based on the continuous variable, with a higher probability of sleep apnea triggering more frequent prompts for screening than for a user with a lower probability of sleep apnea.

In addition to reporting the binary result (or a non-binary result), in some examples, the user can review a report on the data from the screening. In some examples, the report can include data covering both qualifying and non-qualifying nights. In some examples, the report can include the qualifying nights and not include the non-qualifying nights. In some examples, the data buffer (e.g., data buffer 204) can be sized such that it can hold sufficient data for qualifying nights for the multi-night screening. In some examples, the report can include the nightly parameter (either as a continuous variable or a state). In some examples, the report available to a medical professional can include different information. For example, the report visible to a user may include only a nightly parameter representing a state or only the multi-night parameter representing a state, whereas the report for a medical professional can include continuous variables for nightly and/or multi-night parameters.

Figure 4A:
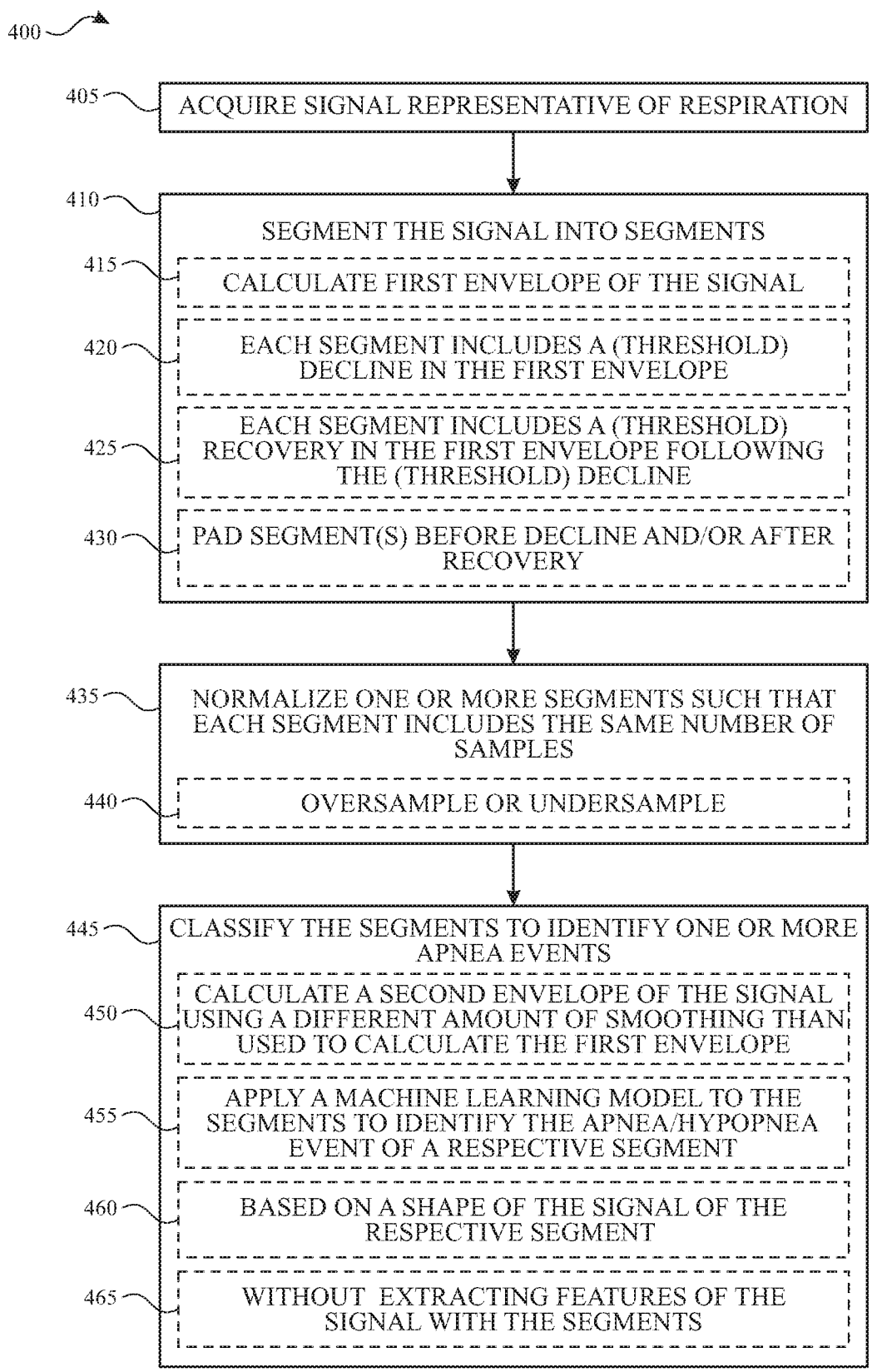
FIGS. 4A-4B illustrate exemplary processes for identifying one or more apnea/hypopnea events based on a respiration signal according to examples of the disclosure.
Figure 4B:
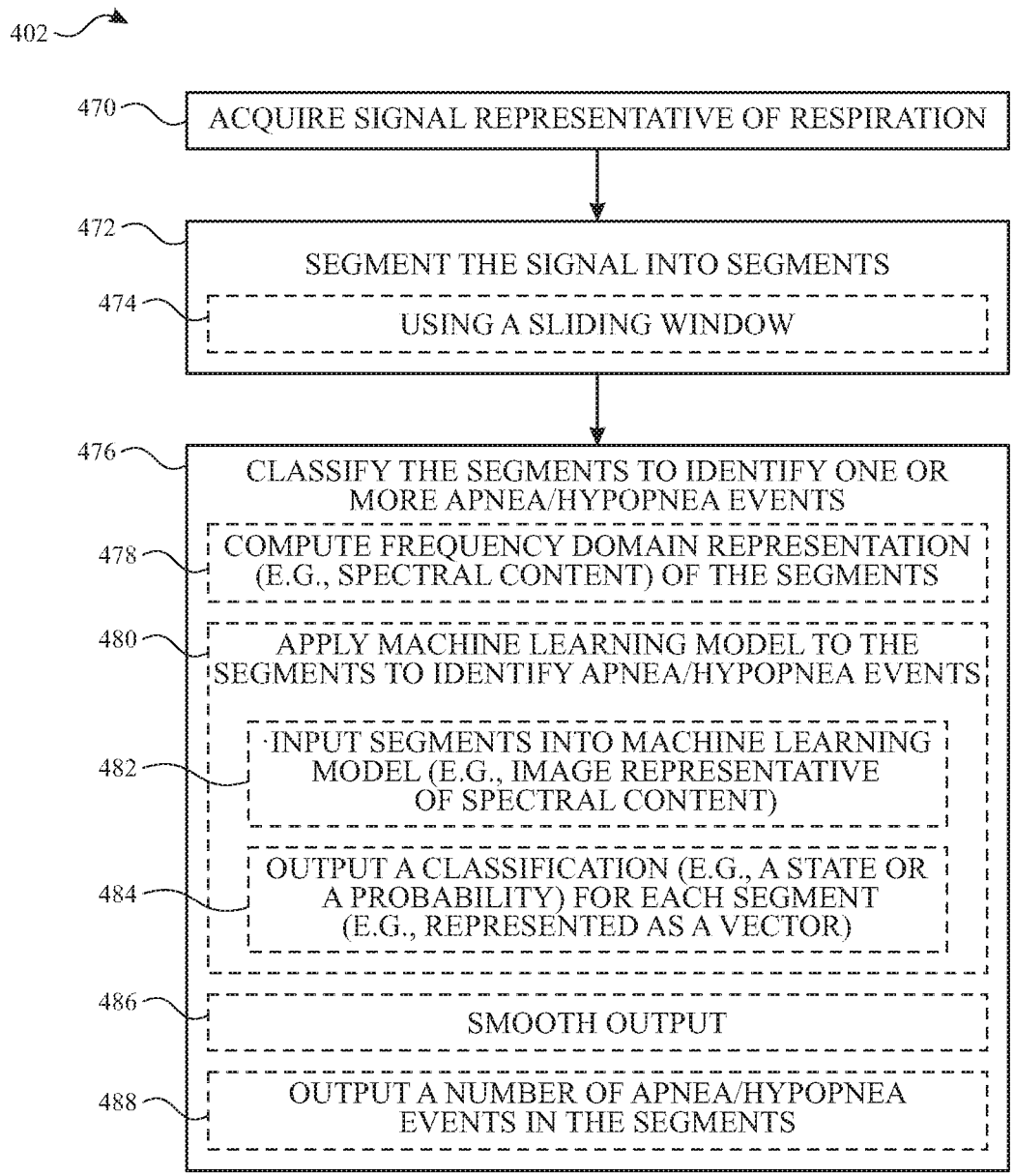

FIGS. 4A-4B illustrate exemplary processes for identifying one or more apnea/hypopnea events based on a respiration signal according to examples of the disclosure. FIG. 4A illustrates an exemplary process 400 for identifying one or more apnea/hypopnea events based on a respiration signal according to examples of the disclosure. At 405, a signal representative of respiration of a user can be acquired (e.g., corresponding to 305 in process 300). At 410, the respiration signal can be segmented into segments. In some examples, the segmentation process can include calculating an envelope of the respiration signal (415). In some examples, the respiration signal can be divided into segments such that each segment includes one dip or decline in the envelope of the respiration signal (420). In some examples, a dip or decline in the envelope of the respiration signal can require a threshold decrease (e.g., 5%) in the envelope from a baseline value (e.g., corresponding to normal respiration without apnea/hypopnea). In some examples, the respiration signal can be divided into segments such that each segment includes one rise or recovery in the envelope of the respiration signal following the dip or decline in the envelope of the respiration signal (425). In some examples, a rise or recovery in the envelope of the respiration can require a threshold increase in the envelope (e.g., to within 5% of the baseline value corresponding to normal respiration without apnea/hypopnea). In some examples, respective segments of the respiration signal can begin at the respective decline identified in the envelope signal for the respective segments. Although the segmentation is described primarily based on an envelope of the respiration signal, it is understood that other characteristics than the envelope of the respiratory signal can be used to segment the respiration signal.

In some examples, the respective segments can be padded with data prior to the respective decline identified in the envelope signal (430). In some examples, the padding can include a portion of the respiration signal prior to the decline (e.g., the raw respiration signal). In some examples, one or more values on the respiration signal prior to the decline can be duplicated and included at the start of the segment. In some examples, a baseline envelope value (e.g., corresponding to normal respiration) can be used to pad the start of the segment prior to the decline. Additionally or alternatively, in some examples, the respective segments can be padded with data after the respective recovery identified in the envelope signal (430). In some examples, the padding can include a portion of the respiration signal after to the recovery (e.g., the raw respiration signal). In some examples, one or more values on the respiration signal after to the recovery can be duplicated and included at the end of the segment after the recovery. In some examples, a baseline envelope value (e.g., corresponding to normal respiration) can be used to pad the end of the segment after the recovery.

The length of segments of the respiration signal resulting from the segmentation at 410 can be of different durations in time (and therefore can including a different number of digitized samples). In some examples, at 435, one or more of segments can be normalized such that each of the segments includes the same number of samples. The normalization of segments can include (440), in some examples, decreasing the size of a segment by down-sampling relatively long duration segments (e.g., larger size compared to the target size of the segments expected by subsequent processing). Additionally or alternatively, in some examples, the normalization of segments can include (440) increasing the size of a segment by up-sampling relatively short duration segments (e.g., smaller size compared to the target size of the segments expected by subsequent processing). Some samples may not require normalization if their duration/size matches the target duration/size prior to normalization at 435.

At 445, the normalized segments can be classified to identify one or more apnea/hypopnea events. In some examples, classification can include calculating a second envelope of the respiration signal (450). The second envelope can be calculated using a different amount of smoothing of the respiration signal compared with the amount of smoothing used to calculate the envelope of the respiration signal for segmentation at 410. For example, the segmentation process at 410 can rely on a first envelope that is smoother than the second envelope. The second envelope can be less smooth to provide more information for use in the actual classification of apnea/hypopnea events. The first envelope, however, can be smoother to avoid segmenting the respiration signal into too small segments (that are more likely to be resultant of noise than another potential breathing related event to classify). In some example, the classification can be achieved by applying, at 455, a machine learning model to the segments. The machine learning model can be implemented in DSP 206 (or other machine learning processing circuitry). The machine learning model can accept each of the segments of the respiration signal as an input, and can output a classification identifying an apnea/hypopnea event or lack thereof for each of the segments. In some examples, the machine learning model can classify the respective segments based on the shape of the respective segment of the respiration signal (460). In some examples, the machine learning model can classify the respective segments without extracting features of respiration signal (465) (e.g., without extracting features such as the magnitude of the decline in the respiration signal amplitude, the duration of a cessation or pause in breathing, the magnitude of the recovery in the respiration signal amplitude, etc.). In some examples, the machine learning model can classify the respective segments using extracted features of respiration signal. The extracted features can include the length of the segment, the number of breaths in the segment, and/or the breath amplitude, among other possible features. In some examples, the machine learning model can also classify the respective segments using information or features from periods before and/or after the respective segment. The machine learning model can be trained using training segments of respiration signals and the corresponding reference scoring (e.g., by a human expert) classification as apnea/hypopnea events or not.

As described herein the machine learning model can be a deep learning model. In some examples, the machine learning model can be implemented using a neural network (e.g., machine learning processing circuit) including one or more convolutional layers. Additionally, in some examples, the neural network can optionally include one or more fully connected layers. In some examples, each of the convolutional layers can convolve the input to the convolutional layer with multiple filters (including filter coefficients that may be set via training). Optionally, each of the convolutional layers can also include a non-linear function layer and/or down-sampling/pooling layer to implement non-linarites and/or simplify the feature set (e.g., change the resolution of the output) before processing by a subsequent layer. In some examples, the output of the one or more convolutional layers can be input to a classification layer. The classification layer can including a flattening later to generate the final feature set and a fully connected layer to map the features to the output classifications. The classification layer can make the decision on whether the segment includes an apnea/hypopnea event. In some examples, the classification layer can include more than one fully connected layer or may include a non-linear function.

Figure 6A:
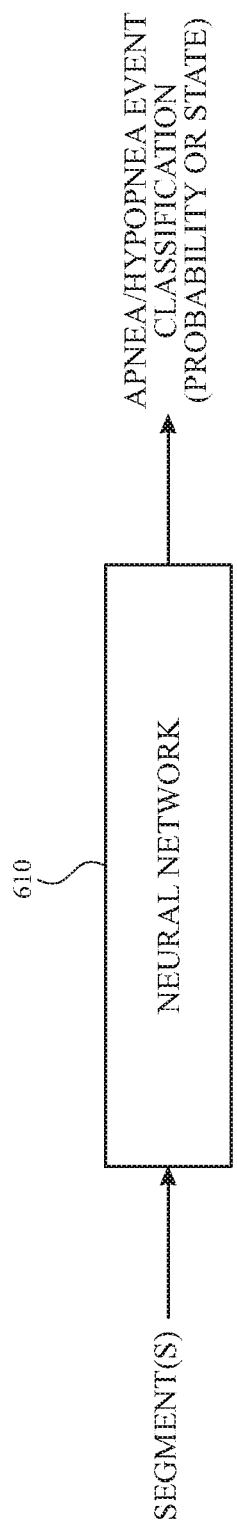
FIGS. 6A-6B illustrate exemplary implementations of a machine learning model according to examples of the disclosure.

FIG. 6A illustrates an exemplary implementation of a machine learning model according to examples of the disclosure. FIG. 6A illustrates a neural network 600 that can, in some examples, be a convolutional neural network (CNN). In some examples, neural network can be a recurrent neural network (RNN), which can include memory (internal states) to track information (e.g., feedback from the output, such as estimation of apnea/hypopnea state from one or more segments of the respiration signal, extracted features, etc.). In some examples, the neural network can include convolutional and recurrent layers. The neural network can accept, as input, each of the segments of the respiration signal, and can output a classification identifying an apnea/hypopnea event or lack thereof for each of the segments as described above (e.g., each segment processed by the machine learning model independently). In some examples, the neural network can accept, as input, multiple segments as a sequence (e.g., the input can include the current segment and one or more prior segments) to allow the neural network to use temporal information from nearby segments for classifying the current segment (e.g., each segment processed by the machine learning model using information about one or more prior and/or future segments). Additionally or alternatively, in some examples, the input to the neural network can include features extracted from respiration signal for each segment of the respiration signal (e.g., the length of the segment, the number of breaths in the segment, and/or the breath amplitude, among other possible features). In some examples, the neural network can also use state information of one or more segments before or after the respective segment (e.g., information or features from periods before and/or after the respective segment). The neural network can be trained using training segments of respiration signals and the corresponding reference classification (e.g., by a human expert) as apnea/hypopnea events or not. It is understood that neural network 600 is one example, but the neural network for classification of apnea/hypopnea events described herein can be achieved using fewer, more and/or different layers in the same or different configurations. In some examples, the machine learning models can be stored in memory (e.g., data buffer/memory 204) and processing circuitry (e.g., DSP 206) can be configured to implement the neural network stored in memory.

In some examples, rather than a machine learning model, the segments can be classified using feature extraction. For example, features such as the magnitude of the decline in the respiration signal amplitude, the duration of a cessation or pause in breathing, the magnitude of the recovery in the respiration signal amplitude, etc., can be extracted and apnea/hypopnea events can be detected based on the magnitude of the decline in respiration (e.g., based on the second envelope calculated from the respiration signal), the magnitude of the recovery of the respiration signal (e.g., based on the second envelope calculated from the respiration signal), and the duration of the pause in respiration therebetween (e.g., a threshold duration of pause).

In some examples, the classification can also include a confidence parameter. For example, whether using the machine learning model for classification based on shape or classification using feature extraction, the output can include a confidence in the classification. For example, some segments that may be easier to classify as apnea/hypopnea or non-apnea/hypopnea events can be provided with a higher confidence. Some segments that may be more difficult to classify as apnea/hypopnea or non-apnea/hypopnea event can be provided a lower confidence. In some examples, the confidence can be based on extracted feature parameters (e.g., magnitude of amplitude drop, duration of pause, etc.).

FIG. 4B illustrates an exemplary process 402 for identifying one or more apnea/hypopnea events based on a respiration signal according to examples of the disclosure. At 470, a signal representative of respiration of a user can be acquired (e.g., corresponding to 305 in process 300). At 472, the respiration signal can be segmented into segments. In some examples, the segmentation process can include dividing the respiration signal into segments of equal length (equal duration in time). In some examples, the segmentation can be achieved using a sliding window over the respiration signal (474). In some examples, the sliding window can result in overlapping segments of the respiration signal. In some examples, the window can be between 10 seconds and 2 minutes in duration. In some examples, the window can be between 5 seconds and 5 minutes in duration. In some examples, the window can be between 15 seconds and 45 seconds. In some examples, the sliding window can shift by 1%-50% between segments. In some examples, the window can shift between 5%-25% between segments. In some examples, the window can shift 10% between segments. In some examples, the windows may be non-overlapping. It should be understood that the above ranges for the window and the amount of sliding/shift between segments are exemplary, and other windows or amounts of sliding/shifting are possible. Segmentation according to process 402 can simplify the processing requirements compared with segmentation according to process 400 (e.g., omitting the processing at 410-440).

At 476, the segments can be classified to identify one or more apnea/hypopnea events. In some examples, classification can include computing a frequency domain representation of the segments (478). In some examples, the frequency domain representation can be computed using a transform technique (e.g., using a fast Fourier transform (FFT) or other suitable technique). In some examples, the frequency domain representation can be the spectral density of the segment. The frequency domain representation can be computed for each of the segments. In some example, the classification can be achieved by applying, at 480, a machine learning model to the segments. The machine learning model can be implemented in DSP 206, for example.

In some examples, at 482, the segments can be input into the machine learning model. The machine learning model can accept the frequency domain representation of the segments of the respiration signal as an input, and can output, at 484, a classification identifying one or more apnea/hypopnea events or lack thereof for the segments. In some examples, the input to the machine learning model may be a temporal sequence of the frequency domain representation of multiple segments (e.g., 100 segments, 500 segments, 1000 segments, 2000 segments, etc.) of the respiration signal. For example, the resulting sequence of frequency domain representations can be considered an input similar to an image (e.g., represented as a matrix) with one axis (e.g., y-axis) representing frequency, one axis representing time or segment number (e.g., x-axis), and values representing the frequency content (e.g., spectral power) of the respiration signal. In some examples, the respiration signal for an entire night (or other period of time) can be divided into multiple images to input into the machine learning model, with each image representing a fixed period of time (e.g., 20 minutes, 30 minutes, 45, minutes, an hour, etc.). In some examples, if there is a remainder of the respiration signal smaller than the duration for an image to input into the machine learning model, the remainder can be discarded. In some examples, the remainder can be normalized or padded to match the size of the input to the machine learning model.

In some examples, the output of the machine learning model can be a state representation of whether an apnea/hypopnea event occurs or not within each segment in an input of multiple segments (in an input image). In some examples, the state representation can be a binary representation classifying a segment as "including an apnea/hypopnea event" or "not including an apnea/hypopnea event" (and optionally these states may be represented with a binary "1" or "0" to indicate state). For example, for N segments, the output of the machine learning model can contain N outputs indicative of the state for each segment. In some examples, the output can be represented as a 1×N vector, where each value in the vector indicates the state for one of the N segments. As a result, this output can provide an indication of the presence of and number of apnea/hypopnea events (at 488) in the multiple segments included in the input of multiple segments (e.g., by counting the number of segments classified as including an apnea/hypopnea event). In addition, the output can be viewed as providing an indication of the timing of apnea/hypopnea events in the input including multiple segments. Additionally or alternatively, in some examples, the machine learning model can output, at 488, a number of apnea/hypopnea events in the input including multiple segments in addition to or instead of the classification of each segment in the input.

In some examples, further processing can be applied to smooth the output at 486. For example, depending on the amount of shift associated with the sliding window, the classification output of multiple adjacent segments may each indicate the same apnea/hypopnea event rather than different apnea/hypopnea events. Without smoothing, in such instances, the output can overestimate the number of apnea/hypopnea events in the input. The likelihood of overestimating the number of apnea/hypopnea events can increase the more the segments overlap. In some examples, the smoothing can include counting consecutive segments with the same classification state of "including an apnea/hypopnea event" as indicating one apnea/hypopnea event. For example, if the output includes a 1×N vector with "1" representing the state of "including an apnea/hypopnea event" and "0" representing the state of "not including an apnea/hypopnea event," consecutive values in the vector of "1" can be merged and counted only once.

In some examples, rather than representing the output for each segment in the input as a binary value, the output can be a probability that the segment includes an apnea/hypopnea event (e.g., between 0 and 1). In some cases, a threshold can be set comparing the probability to a threshold separating between the corresponding states. For example, the threshold can be set at 0.5 and when the probability for a segment is greater than the threshold, the state can be determined to be "including an apnea/hypopnea event" and when the probability for the segment is less than the threshold, the state can be determined to be "not including an apnea/hypopnea event." In some examples, after applying the threshold to the output, the output can be smoothed using the smoothing described above. In some examples, smoothing can be performed before applying the threshold. For example, the probabilities of an apnea/hypopnea event for the multiple segments can be smoothed using a sliding window (e.g., a moving average or other suitable smoothing technique), and the threshold can be applied after smoothing the probabilities to yield a state representation for the multiple segments. In some examples, the number of apnea/hypopnea events can then be counted (optionally counting adjacent and contiguous segments with a state "including an apnea/hypopnea event" as single apnea/hypopnea events). In some examples, the smoothing/counting described above can be performed without generating a state representation (e.g., counting the number of segments with a probability above the threshold, where adjacent and contiguous segments with a probability above the threshold are counted as single apnea/hypopnea events).

In some examples, a probabilistic decoder (e.g., a Viterbi decoder) can be used compute the number of apnea/hypopnea events. For example, the output of the machine learning model can include a probability of each segment being in one of two states, apnea/hypopnea, or no apnea/hypopnea, such that the probabilities sum to 1 (e.g., a 2×N vector of probabilities). A state transition matrix can be learned from training data to indicate the probability of being in a particular state (apnea/hypopnea, or no apnea/hypopnea) given the previous state (e.g., a 2×2 matrix of transition probabilities). A probabilistic decoder (e.g., a Viterbi decoder) can be applied using the state transition matrix and the state probability outputs to compute an updated set of state probabilities that considers the temporal context of each segment. A threshold can be applied to the updated probabilities, and the number of apneas or hypopneas can be determined from the resulting binary sequence.

Figure 6B:
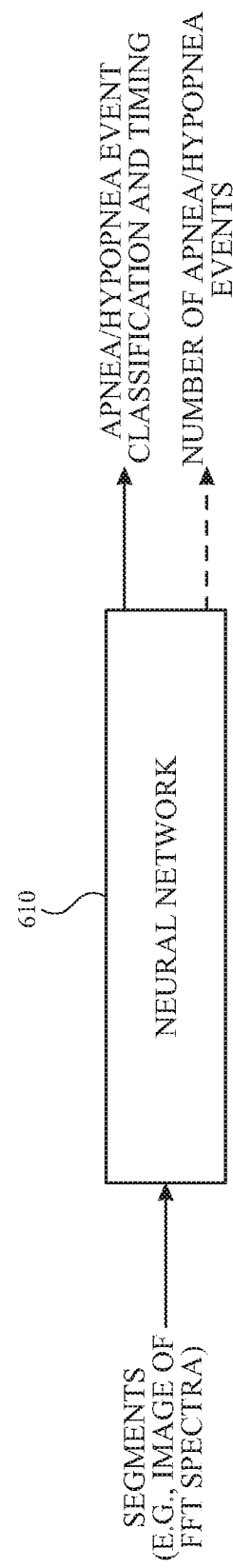

As described herein the machine learning model can be a deep learning model. In some examples, the machine learning model can be implemented using a neural network (e.g., machine learning processing circuit) including one or more convolutional layers and one or more fully connected layers. FIG. 6B illustrates an exemplary implementation of a machine learning model according to examples of the disclosure. FIG. 6B illustrates a neural network 610 that can, in some examples, be a CNN or RNN (e.g., using long short term memory (LTSM)). The neural network can accept, as input, multiple overlapping segments of the respiration signal (FFT spectral images where spectra of multiple overlapping segments can be treated as an image with one axis representing time/segment, one axis representing frequency, and the value representing spectral power), and can output a classification identifying an apnea/hypopnea event or lack thereof for the multiple segments. Convolutional layers of neural network 610 can be used to extract features from the input (e.g., from the FFT spectral image). In some examples, the output can include a 1×N vector indicating the state for the N segments (and providing a timing of the apnea/hypopnea events). Additionally or alternatively, in some examples, the output of the neural network can include a number of apnea/hypopnea events in the multiple input segments. In some examples, the number of apnea/hypopnea events can be computed from the 1×N vector by counting the apnea/hypopnea events.

In some examples, the neural network can be trained using training images representing multiple overlapping segments of a respiration signal and the corresponding representations of the occurrence and timing of apnea/hypopnea events (e.g., a 1×N vector). In some examples, the neural network can be trained using training images representing multiple overlapping segments of a respiration signal and numbers of apnea/hypopnea events in the training images. In some examples, the training data can include both a representation of the occurrence and timing of apnea/hypopnea events (e.g., the 1×N vector) and a number of apnea/hypopnea events in each of the training images (using two outputs), and both pieces of information may be used simultaneously to train a neural network (multi-task learning). In some examples, after training the neural network using two outputs (for each input), a number of apnea/hypopnea events for an input image can be computed (e.g., counted) from the representation of the timing of apnea/hypopnea event (the first output) to estimate a parameter representative of apnea/hypopnea events per duration corresponding to the input image. In some examples, after training the neural network using two outputs (for each input), a number of apnea/hypopnea events for an input image can be determined as the number of apnea/hypopnea events output of the neural network (the second output) to estimate a parameter representative of apnea/hypopnea events per duration corresponding to the input image. In some examples, training the neural network using two outputs simultaneously can improve the performance of the neural network, but only one of output may be used estimate a parameter representative of apnea/hypopnea events per duration corresponding to the input image (e.g., the output with superior accuracy). It is understood that neural network 610 is one example, but the neural network for classification of apnea/hypopnea events described herein can be achieved using different configurations. In some examples, the machine learning models can be stored in memory (e.g., data buffer/memory 204) and processing circuitry (e.g., DSP 206) can be configured to implement the neural network stored in memory.

The number of apnea/hypopnea events can be summed (for one or more images corresponding to one or more groups of segments) and divided by total duration represented by the input segments to yield an estimate of a nightly parameter indicative of a severity of (or presence of) sleep apnea.

Figure 5:
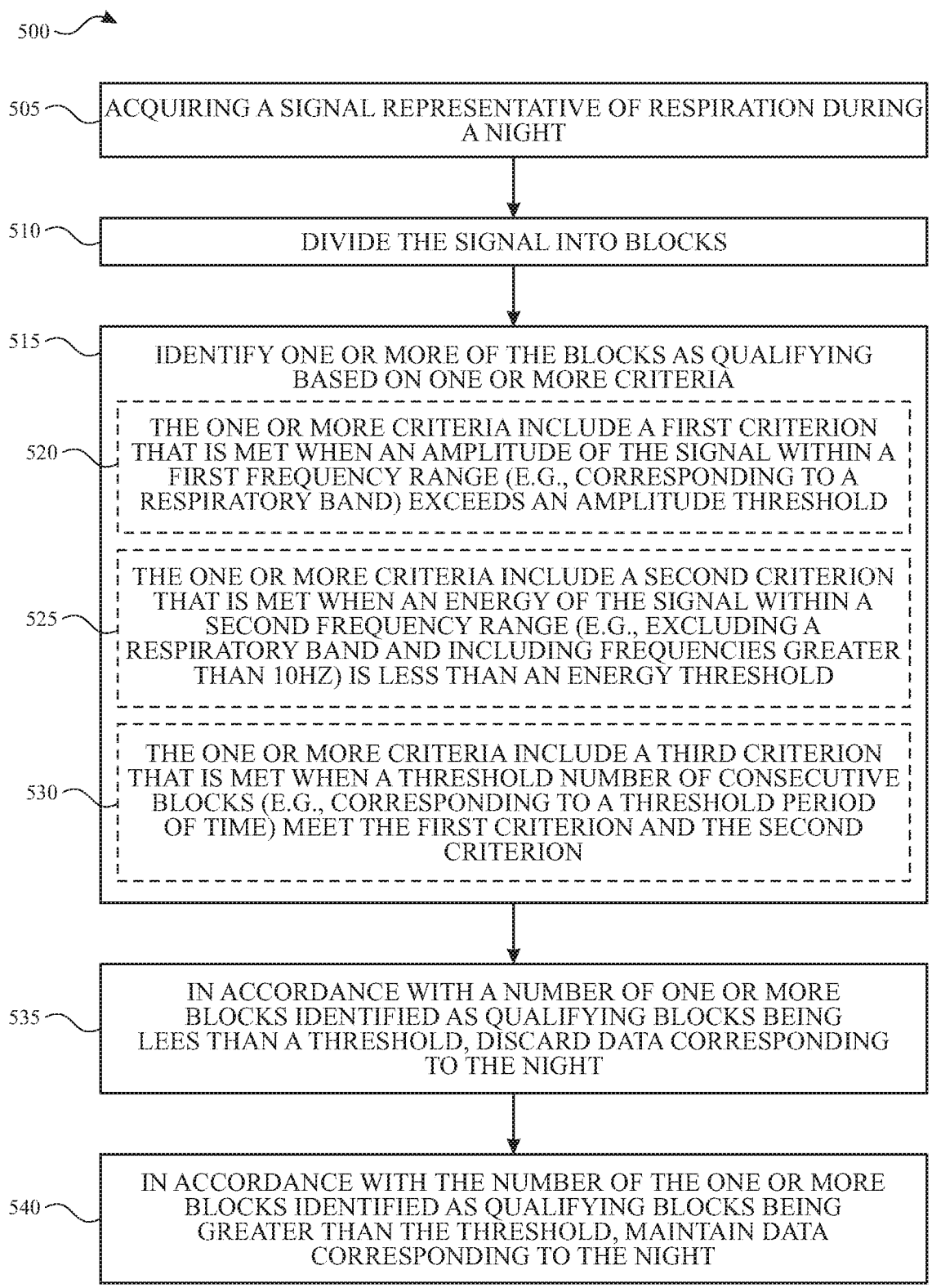
FIG. 5 illustrates an exemplary process for performing quality checks according to examples of the disclosure.

FIG. 5 illustrates an exemplary process 500 for performing quality checks according to examples of the disclosure. At 505, a signal representative of respiration of a user for a period of time (e.g., a night) can be acquired (e.g., corresponding to 305 in process 300, corresponding to 405 in process 400, or corresponding to 476 in process 402). At 510, the respiration signal can be divided into blocks (i.e., segments of time). In some examples, the division of the respiration signal at 510 can be different from the segmentation at 410 or 472. The division of the respiration signal at 510 can divide the respiration signal into blocks of time of different (larger) duration than the segments and based on different criteria. For example, rather than segmenting the respiration signal based on features of an envelope of the respiration signal, the respiration signal can be divided based on time/duration. For example, each of the blocks can correspond to a block of time of a predetermined duration (e.g., 5 minutes, 10 minutes, 15 minutes, 30 minutes, etc.). In some examples, the predetermined duration can be the same duration as the duration corresponding to the input image described with respect to process 402.

At 515, one or more of the blocks can be identified as qualifying (or not qualifying) based on one or more criteria. In some examples, the criteria can include a criterion related to respiration signal amplitude. For example, the criterion can be met when the amplitude of the respiration signal within a first frequency range is greater than an amplitude threshold (520). For example, the respiration signal for the block can be filtered with one or more low pass filters a representation of signal amplitude for the block can be calculated. In some examples, a first low pass filter can be applied to isolate the respiratory band of frequencies of the acquired respiration signal. In some examples, an absolute value of the low-pass-filtered respiration signal can be taken, and then a second low pass filter can be applied. In some examples, the representation of the signal amplitude for the block can be calculated by taking a mean of the respiration signal for the block of time (e.g., after applying the first low pass filter, the absolute value function and a second low pass filter). In some examples, rather than a mean, a mode, weighted average or median amplitude can be calculated to represent the signal amplitude for the block. It should be understood that other calculations can be used to represent the signal amplitude for the block. The calculated representation of the signal amplitude for the block can be compared with the amplitude threshold. The criterion can be unmet when the amplitude of the respiration signal within the first frequency range is less than the amplitude threshold. The first frequency range can correspond to the respiratory band (e.g., less than 1 Hz).

In some examples, the criteria can include a criterion related to noise in the respiration signal. For example, the criterion can be met when the energy of the respiration signal within a second frequency range is less than an energy threshold (525). For example, the energy of the respiration signal within the second frequency range can be calculated by computing frequency content of the block (e.g., using a fast Fourier transform) and then computing the power in the frequencies within the second frequency range. The criterion can be unmet when the energy of the respiration signal within the second frequency range is greater than the energy threshold. The second frequency range can correspond to the frequencies outside the respiratory band. In some examples, the second frequency range can be between 10-500 Hz. In some examples, the second frequency range can be between 20-100 Hz.

In some examples, rather than using a separate signal criterion and a separate noise criterion described above, a signal-to-noise criterion can be used. For example, a signal-to-noise ratio can be computed (e.g., using the above algorithms) and the calculated signal-to-noise ratio can be compared with a signal-to-noise threshold. The criterion can be met when the signal-to-noise ratio of the respiration signal of the block is greater than an SNR threshold, and the criterion can be unmet when the signal-to-noise ratio of the respiration signal is less than the SNR threshold.

In some examples, the criteria can include a criterion related to the detected sleep state of the user. For example, an apnea-hypopnea index for screening for sleep apnea may be calculated using respiratory events that occur during sleep. As a result, discarding the respiratory signal during the awake state can be desirable. In some examples, the sensor (e.g. sensor strip 180) and accompanying processing can be used to estimate a sleep stage of a user. In some examples, the sleep stage can include a sleep state and an awake stage. In such examples, blocks (or segments within a block) acquired while the user is in an awake state can be discarded (or not used for processing) and blocks (or segments within a block) acquired while the user is in a sleep state can be used.

In some examples, the criteria can include a criterion related to continuity of respiration signal quality. For example, the criterion can be met when a threshold number of consecutive blocks meet the signal amplitude criterion and noise energy criterion (530). The threshold number of consecutive blocks can correspond to a threshold period of time. For example, for 5-minute blocks and a 20-minute threshold period of time, four consecutive blocks meeting the signal amplitude criterion and noise energy criterion can be required for the four blocks to contribute to toward quality sleep blocks. The criterion can be unmet when less than the threshold number of consecutive blocks meet the signal amplitude criterion and noise energy criterion. For example, for 10-minute blocks and a 30-minute threshold period of time, a single block or two consecutive blocks would be not meet the threshold and therefore would not contribute toward quality sleep blocks.

In some examples, a night can be considered a qualifying night if a threshold number of qualifying sleep blocks (or a total amount of quality sleep time in a night) meet a threshold. At 535, in accordance with a number of the one or more blocks identified as qualifying blocks being less than a threshold (for a night), the night can be considered non-qualifying. The data for the night can be discarded and/or it can be excluded from consideration for assessing a sleep condition. At 540, in accordance with the number of the one or more blocks identified as qualifying blocks being greater than the threshold (for a night), the night can be considered qualifying. The data for the night can be maintained and/or can be included for assessing the sleep condition (e.g., at 380). In some examples, the threshold for a night can be set to correspond to a minimum period of time. The minimum period of time can, in some examples, correspond to four hours of qualifying sleep time including groups of consecutive periods of sleep in which the respiration signal meets both the signal amplitude criterion and noise energy criterion.

After performing quality checks described above and with respect to FIG. 5, the data for a qualifying night can be processed (e.g., according to process 350). In some examples, the processing (e.g., according to process 350) can be applied only to qualifying blocks from a qualifying night.

As discussed above, aspects in of the present technology include the gathering and use of physiological information. The technology may be implemented along with technologies that involve gathering personal data that relates to the user's health and/or uniquely identifies or can be used to contact or locate a specific person. Such personal data can include demographic data, date of birth, location-based data, telephone numbers, email addresses, home addresses, and data or records relating to a user's health or level of fitness (e.g., vital signs measurements, medication information, exercise information, etc.).

The present disclosure recognizes that a user's personal data, including physiological information, such as data generated and used by the present technology, can be used to the benefit of users. For example, assessing a user's sleep conditions (e.g., to screen for moderate-to-severe sleep apnea) may allow a user to track or otherwise gain insights about their health.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates embodiments in which users selectively block the collection of, use of, or access to, personal data, including physiological information. For example, a user may be able to disable hardware and/or software elements that collect physiological information. Further, the present disclosure contemplates that hardware and/or software elements can be provided to prevent or block access to personal data that has already been collected. Specifically, users can select to remove, disable, or restrict access to certain health-related applications collecting users' personal health or fitness data.

Therefore, according to the above, some examples of the disclosure are directed to a method. The method can comprise: acquiring a signal representative of respiration; segmenting the signal into segments, wherein a first of the segments includes a different number of sample than a second of the segments; normalizing one or more of the segments such that each of the segments includes the same number of samples; and classifying the segments to identify one or more apnea/hypopnea events. Additionally or alternatively to one or more of the examples disclosed above, in some examples, segmenting the signal into segments can comprise: calculating a first envelope of the signal. Each segment can include a threshold decline in the first envelope. Additionally or alternatively to one or more of the examples disclosed above, in some examples, each segment can include a threshold recovery in the first envelope following the threshold decline in the first envelope. Additionally or alternatively to one or more of the examples disclosed above, in some examples, segmenting the signal into segments can further comprise padding a respective one of the segments with one or more samples corresponding to the signal before the threshold decline in the first envelope or padding the respective one of the segments with one or more samples corresponding to the signal after the threshold recovery in the first envelope. Additionally or alternatively to one or more of the examples disclosed above, in some examples, segmenting the signal into segments can further comprise padding a respective one of the segments with one or more samples corresponding to the signal before the threshold decline in the first envelope. Additionally or alternatively to one or more of the examples disclosed above, in some examples, classifying the segments to identify one or more apnea/hypopnea events can comprise calculating a second envelope of the signal, the second envelope calculated using a different amount of smoothing than the first envelope. Additionally or alternatively to one or more of the examples disclosed above, in some examples, classifying the segments to identify one or more apnea/hypopnea events can comprise applying a machine learning model to the segments to identify an apnea/hypopnea event in a respective segment based on a shape of the signal of the respective segment. Additionally or alternatively to one or more of the examples disclosed above, in some examples, classifying the segments to identify one or more apnea/hypopnea events can comprise applying a machine learning model to the segments without extracting features of the signal in the segments.

Some examples of the disclosure are directed to a non-transitory computer readable storage medium. The non-transitory computer readable storage medium can store instructions (e.g., one or more programs), which when executed by one or more processing circuits can cause the electronic device to perform any of the above methods.

Some examples of the disclosure are directed to an electronic device. The electronic device can comprise one or more processing circuits, memory (e.g., a non-transitory computer readable storage medium), and one or more programs. The one or more programs can be stored in the memory and can be configured to be executed by the one or more processing circuits. The one or more programs can include instructions for performing any of the above methods. Additionally or alternatively to one or more of the examples disclosed above, in some examples, the device can further comprise communication circuitry configured to receive one or more signals representative of respiration from a physiological signal sensor. Additionally or alternatively to one or more of the examples disclosed above, in some examples, the physiological signal sensor can comprise a sensor strip including a plurality of piezoelectric sensors. Additionally or alternatively to one or more of the examples disclosed above, in some examples, the device can further comprise a display configured to display a sleep apnea screening result.

Some examples of the disclosure are directed to an electronic device. The electronic device can comprise a physiological signal sensor and processing circuitry in communication with the physiological signal sensor. The processing circuitry can be configured to (e.g., programmed to) perform any of the above methods.

Some examples of the disclosure are directed to a method. The method can comprise: acquiring a signal representative of respiration during a threshold period of time; dividing the signal into blocks; identifying one or more of the blocks as qualifying based on one or more criteria; in accordance with a number of one or more blocks identified as qualifying blocks being less than a threshold, discarding (or not using) data corresponding to the threshold period of time; and in accordance with the number of the one or more blocks identified as qualifying blocks being greater than the threshold, maintaining (or using) data corresponding to the threshold period of time. Additionally or alternatively to one or more of the examples disclosed above, in some examples, the one or more criteria can include a first criterion that can be met when an amplitude of the signal within a first frequency range exceeds an amplitude threshold. Additionally or alternatively to one or more of the examples disclosed above, in some examples, the first frequency range can correspond to a respiratory band. Additionally or alternatively to one or more of the examples disclosed above, in some examples, the one or more criteria can include a second criterion that can be met when an energy of the signal within a second frequency range is less than an energy threshold. Additionally or alternatively to one or more of the examples disclosed above, in some examples, the second frequency range can exclude a respiratory band and includes frequencies greater than 10 Hz. Additionally or alternatively to one or more of the examples disclosed above, in some examples, the one or more criteria can include a third criterion that can be met when a threshold number of consecutive blocks meet the first criterion and the second criterion. Additionally or alternatively to one or more of the examples disclosed above, in some examples, the threshold number of consecutive blocks can correspond to 30 minutes of time. Additionally or alternatively to one or more of the examples disclosed above, in some examples, the threshold can correspond to 4 hours of time.

Some examples of the disclosure are directed to a non-transitory computer readable storage medium. The non-transitory computer readable storage medium can store instructions (e.g., one or more programs), which when executed by one or more processing circuits can cause the electronic device to perform any of the above methods.

Some examples of the disclosure are directed to an electronic device. The electronic device can comprise one or more processing circuits, memory (e.g., a non-transitory computer readable storage medium), and one or more programs. The one or more programs can be stored in the memory and can be configured to be executed by the one or more processing circuits. The one or more programs can include instructions for performing any of the above methods. Additionally or alternatively to one or more of the examples disclosed above, in some examples, the device can further comprise communication circuitry configured to receive one or more signals representative of respiration from a physiological signal sensor. Additionally or alternatively to one or more of the examples disclosed above, in some examples, the physiological signal sensor can comprise a sensor strip including a plurality of piezoelectric sensors. Additionally or alternatively to one or more of the examples disclosed above, in some examples, the device can further comprise a display configured to display a sleep apnea screening result.

Some examples of the disclosure are directed to an electronic device. The electronic device can comprise a physiological signal sensor and processing circuitry in communication with the physiological signal sensor. The processing circuitry can be configured to (e.g., programmed to) perform any of the above methods.

Some examples of the disclosure are directed to a method. The method can comprise: segmenting a signal representative of respiration into segments; computing frequency domain representations of the segments; generating an input image from the frequency domain representations of the segments; and classifying the segments to identify one or more apnea/hypopnea events. Classifying the segments to identify one or more apnea/hypopnea events can comprise applying a machine learning model to the input image to identify an apnea/hypopnea event in the segments. Additionally or alternatively to one or more of the examples disclosed above, in some examples, computing the frequency domain representations of the segments can comprise computing fast Fourier transforms (FFTs) of the segments. Additionally or alternatively to one or more of the examples disclosed above, in some examples, the segmentation of the signal can be performed using a sliding window such that the segments overlap. Additionally or alternatively to one or more of the examples disclosed above, in some examples, classifying the segments to identify one or more apnea/hypopnea event can further comprise smoothing an output of the machine learning model. Additionally or alternatively to one or more of the examples disclosed above, in some examples, the output of the machine learning model can include\a representation, for each respective segment of the segments, of a probability that the respective segment includes an apnea/hypopnea event. Smoothing can comprise counting adjacent and contiguous values in the representation with the probability above a threshold as single apnea/hypopnea events. Additionally or alternatively to one or more of the examples disclosed above, in some examples, the output of the machine learning model can include a representation, for each respective segment of the segments, of a state of the respective segment as indicative of an apnea/hypopnea event or not. Smoothing can comprise counting adjacent and contiguous segments with the state indicative of the apnea/hypopnea event as single apnea/hypopnea events. Additionally or alternatively to one or more of the examples disclosed above, in some examples, the output of the machine learning model can include a representation, for each respective segment of the segments, of a probability that the respective segment includes an apnea/hypopnea event. Smoothing can comprise applying a probabilistic decoder to the representation to determine a number of apnea/hypopnea events. Additionally or alternatively to one or more of the examples disclosed above, in some examples, the input image generated from the frequency domain representations of the segments can comprise values of spectral content indexed according to frequency and according to timing of the segments.

Some examples of the disclosure are directed to a non-transitory computer readable storage medium. The non-transitory computer readable storage medium can store instructions (e.g., one or more programs), which when executed by one or more processing circuits can cause the electronic device to perform any of the above methods.

Some examples of the disclosure are directed to an electronic device. The electronic device can comprise one or more processing circuits, memory (e.g., a non-transitory computer readable storage medium), and one or more programs. The one or more programs can be stored in the memory and can be configured to be executed by the one or more processing circuits. The one or more programs can include instructions for performing any of the above methods. Additionally or alternatively to one or more of the examples disclosed above, in some examples, the device can further comprise communication circuitry configured to receive one or more signals representative of respiration from a physiological signal sensor. Additionally or alternatively to one or more of the examples disclosed above, in some examples, the physiological signal sensor can comprise a sensor strip including a plurality of piezoelectric sensors. Additionally or alternatively to one or more of the examples disclosed above, in some examples, the device can further comprise a display configured to display a sleep apnea screening result.

Some examples of the disclosure are directed to an electronic device. The electronic device can comprise a physiological signal sensor and processing circuitry in communication with the physiological signal sensor. The processing circuitry can be configured to (e.g., programmed to) perform any of the above methods.

Some examples of the disclosure are directed to a method. The method can comprise: acquiring a plurality of signals representative of respiration for a plurality of periods of time; classifying the plurality of signals to identify one or more apnea/hypopnea events for each of the plurality of periods of time; estimating a parameter representative of severity of apnea/hypopnea for each of the plurality of periods of time; and in accordance with a determination that the parameter representative of severity of apnea/hypopnea is estimated for a threshold number periods of time, estimating a parameter representative of severity of apnea/hypopnea for the plurality of periods of time. Additionally or alternatively to one or more of the examples disclosed above, in some examples, the method further comprises: in accordance with a determination that the parameter representative of severity of apnea/hypopnea is estimated for less than the threshold number periods of time, forgoing estimating the parameter representative of severity of apnea/hypopnea for the plurality of periods of time. Additionally or alternatively to one or more of the examples disclosed above, in some examples, the method further comprising: determining, for each respective signal of the plurality of signals representative of respiration, whether the respective respiration signal satisfies one or more criteria. Classifying the plurality of signals to identify the one or more apnea/hypopnea events for each of the plurality of periods of time can comprise, for each respective signal of the plurality of signals: in accordance with a determination that one or more blocks of the respective respiration signal satisfy the one or more criteria, classifying the one or more blocks of the respective respiration signal; and in accordance with a determination that the one or more blocks of the respective respiration signal fail to satisfy the one or more criteria, forgoing classifying the one or more blocks of the respective respiration signal. Additionally or alternatively to one or more of the examples disclosed above, in some examples, the periods of time can correspond to nights and the threshold number corresponds to seven nights.

Some examples of the disclosure are directed to a non-transitory computer readable storage medium. The non-transitory computer readable storage medium can store instructions (e.g., one or more programs), which when executed by one or more processing circuits can cause the electronic device to perform any of the above methods.

Some examples of the disclosure are directed to an electronic device. The electronic device can comprise one or more processing circuits, memory (e.g., a non-transitory computer readable storage medium), and one or more programs. The one or more programs can be stored in the memory and can be configured to be executed by the one or more processing circuits. The one or more programs can include instructions for performing any of the above methods. Additionally or alternatively to one or more of the examples disclosed above, in some examples, the device can further comprise communication circuitry configured to receive one or more signals representative of respiration from a physiological signal sensor. Additionally or alternatively to one or more of the examples disclosed above, in some examples, the physiological signal sensor can comprise a sensor strip including a plurality of piezoelectric sensors. Additionally or alternatively to one or more of the examples disclosed above, in some examples, the device can further comprise a display configured to display a sleep apnea screening result.

Some examples of the disclosure are directed to an electronic device. The electronic device can comprise a physiological signal sensor and processing circuitry in communication with the physiological signal sensor. The processing circuitry can be configured to (e.g., programmed to) perform any of the above methods.

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

The invention claimed is:

1. An electronic device comprising:
one or more processing circuits;
memory; and
one or more programs, wherein the one or more programs are stored in the memory and configured to be executed by the one or more processing circuits, the one or more programs including instructions for:
    segmenting a signal representative of respiration into segments that are equal in length using a sliding window such that the segments overlap;
    computing frequency domain representations of the segments;
    generating an input image from the frequency domain representations of the segments; and
    classifying the segments to identify one or more apnea/hypopnea events, wherein classifying the segments to identify the one or more apnea/hypopnea events comprises applying a machine learning model to the input image to identify the one or more apnea/hypopnea events in the segments.

2. The device of claim 1, further comprising:
communication circuitry configured to receive the signal representative of respiration from a physiological signal sensor.

3. The device of claim 2, wherein the signal representative of respiration is received from the physiological signal sensor comprising a sensor strip including a plurality of piezoelectric sensors.

4. The device of claim 1, further comprising a display configured to display a sleep apnea screening result.

5. The device of claim 1, wherein computing the frequency domain representations of the segments comprises:
computing fast Fourier transforms (FFTs) of the segments.

6. The device of claim 1, wherein classifying the segments to identify the one or more apnea/hypopnea events further comprises:
smoothing an output of the machine learning model.

7. The device of claim 6, wherein the output of the machine learning model includes a representation, for each respective segment of the segments, of a probability that the respective segment includes an apnea/hypopnea event, and wherein smoothing comprises:
counting adjacent and contiguous values in the representation with the probability above a threshold as single apnea/hypopnea events.

8. The device of claim 6, wherein the output of the machine learning model includes a representation, for each respective segment of the segments, of a state of the respective segment as indicative of an apnea/hypopnea event or not, and wherein smoothing comprises:
counting adjacent and contiguous segments with the state indicative of the apnea/hypopnea event as single apnea/hypopnea events.

9. The device of claim 6, wherein the output of the machine learning model includes a representation, for each respective segment of the segments, of a probability that the respective segment includes an apnea/hypopnea event, and wherein smoothing comprises:
applying a probabilistic decoder to the representation to determine a number of apnea/hypopnea events.

10. The device of claim 1, wherein the input image generated from the frequency domain representations of the segments comprises values of spectral content indexed according to frequency and according to timing of the segments.

11. The device of claim 1, wherein generating the input image comprises generating the input image without extracting features of the signal representative of respiration.

12. The device of claim 1, wherein the signal representative of respiration is a signal from an accelerometer.

13. A method comprising:
segmenting a signal representative of respiration into segments that are equal in length using a sliding window such that the segments overlap;
computing frequency domain representations of the segments;
generating an input image from the frequency domain representations of the segments; and
classifying the segments to identify one or more apnea/hypopnea events, wherein classifying the segments to identify the one or more apnea/hypopnea events comprises applying a machine learning model to the input image to identify the one or more apnea/hypopnea events in the segments.

14. The method of claim 13, wherein computing the frequency domain representations of the segments comprises:
computing fast Fourier transforms (FFTs) of the segments.

15. The method of claim 13, wherein classifying the segments to identify the one or more apnea/hypopnea events further comprises:
smoothing an output of the machine learning model.

16. The method of claim 15, wherein the output of the machine learning model includes a representation, for each respective segment of the segments, of a probability that the respective segment includes an apnea/hypopnea event, and wherein smoothing comprises:
counting adjacent and contiguous values in the representation with the probability above a threshold as single apnea/hypopnea events.

17. The method of claim 15, wherein the output of the machine learning model includes a representation, for each respective segment of the segments, of a state of the respective segment as indicative of an apnea/hypopnea event or not, and wherein smoothing comprises:
counting adjacent and contiguous segments with the state indicative of the apnea/hypopnea event as single apnea/hypopnea events.

18. The method of claim 15, wherein the output of the machine learning model includes a representation, for each respective segment of the segments, of a probability that the respective segment includes an apnea/hypopnea event, and wherein smoothing comprises:
applying a probabilistic decoder to the representation to determine a number of apnea/hypopnea events.

19. The method of claim 13, wherein the input image generated from the frequency domain representations of the segments comprises values of spectral content indexed according to frequency and according to timing of the segments.

20. The method of claim 13, wherein generating the input image comprises generating the input image without extracting features of the signal representative of respiration.

21. A non-transitory computer readable storage medium storing instructions, which when executed by one or more processing circuits, cause the one or more processing circuits to:
segment a signal representative of respiration into segments that are equal in length using a sliding window such that the segments overlap;
compute frequency domain representations of the segments;
generate an input image from the frequency domain representations of the segments; and
classify the segments to identify one or more apnea/hypopnea events, wherein classifying the segments to identify the one or more apnea/hypopnea events comprises applying a machine learning model to the input image to identify the one or more apnea/hypopnea events in the segments.

22. The non-transitory computer readable storage medium of claim 21, wherein generating the input image comprises generating the input image without extracting features of the signal representative of respiration.

23. The non-transitory computer readable storage medium of claim 21, wherein computing the frequency domain representations of the segments comprises:
computing fast Fourier transforms (FFTs) of the segments.

* * * * *